(12) United States Patent
Goh et al.

(10) Patent No.: US 7,650,498 B2
(45) Date of Patent: Jan. 19, 2010

(54) SECURE DATA PROVISION METHOD AND APPARATUS AND DATA RECOVERY METHOD AND SYSTEM

(75) Inventors: Cheh Goh, Singapore (SG); Liqun Chen, Bristol (GB)

(73) Assignee: Hewlett-Packard Development Company, L.P., Houston, TX (US)

( * ) Notice: Subject to any disclaimer, the term of this patent is extended or adjusted under 35 U.S.C. 154(b) by 1011 days.

(21) Appl. No.: 10/825,596

(22) Filed: Apr. 14, 2004

(65) Prior Publication Data

US 2005/0010760 A1 Jan. 13, 2005

(30) Foreign Application Priority Data

Apr. 17, 2003 (GB) ................................. 0308891.1
May 29, 2003 (GB) ................................. 0312235.5

(51) Int. Cl.
*H04L 29/06* (2006.01)
*G06F 7/04* (2006.01)

(52) U.S. Cl. ......................................... 713/161; 726/18
(58) Field of Classification Search .................. 713/161; 726/18
See application file for complete search history.

(56) References Cited

U.S. PATENT DOCUMENTS

| | | | | |
|---|---|---|---|---|
| 5,369,707 | A | 11/1994 | Follendore, III | 380/25 |
| 6,073,242 | A | 6/2000 | Hardy et al. | 713/201 |
| 7,353,395 | B2 * | 4/2008 | Gentry et al. | 713/171 |
| 2003/0033495 | A1 | 2/2003 | Lawman et al. | 711/163 |
| 2003/0055824 | A1 | 3/2003 | Califano | 707/9 |
| 2003/0081785 | A1 * | 5/2003 | Boneh et al. | 380/277 |
| 2003/0179885 | A1 * | 9/2003 | Gentry et al. | 380/277 |
| 2004/0098589 | A1 * | 5/2004 | Appenzeller et al. | 713/170 |
| 2004/0151308 | A1 * | 8/2004 | Kacker et al. | 380/30 |
| 2004/0179684 | A1 * | 9/2004 | Appenzeller et al. | 380/44 |

FOREIGN PATENT DOCUMENTS

| | | |
|---|---|---|
| EP | 0 762 289 A3 | 3/1997 |
| WO | WO 03017559 * | 2/2003 |

OTHER PUBLICATIONS

Boneh, D. and M. Franklin, "Identity-Based Encryption from the Weil Pairing," *in Advances in Crytology-CRYPTO 2001*, LNCS 2139, 31 pages, Springer-Verlag (2001).
Boneh, D., et al., "Identity-Based Mediated RSA," *3rd Workshop on Information Security Application*, Jeju Island, Korea, Aug. 2002. (12 pages).
Cocks, C., "An Identity Based Encryption Scheme Based on Quadratic Residues," *Proceedings of the 8th IMA International Conference on Cryptography and Coding*, LNCS 2260, pp. 360-363, Springer-Verlag, (2001).
Trusted Computing Platform Alliance, TCPA PC Specific Implementation Specification Version 1.00, pp. 1-70 (Sep. 9, 2001).

* cited by examiner

*Primary Examiner*—Matthew B Smithers
*Assistant Examiner*—Techane J Gergiso

(57) ABSTRACT

To control access to target data whilst relieving the data provider of policing obligations, the data provider provides the target data in encrypted form to a requesting party as part of a data set with which first and second trusted authorities are associated in a non-subvertible manner. Recovery of the target data in clear by the party requires the first trusted authority to verify that a specific individual is a professional accredited with it, the second trusted authority to verify that a particular organisation is accredited with it, the particular organisation to verify that the specific individual is engaged by it, and at least one of the particular organisation and the first trusted authority to verify that the party is the specific individual. Various ways of encrypting the target data are provided, the preferred ways being based on Identifier-Based Encryption schemas.

22 Claims, 9 Drawing Sheets

SECURE DATA PROVISION METHOD AND APPARATUS AND DATA RECOVERY METHOD AND SYSTEM

FIELD OF THE INVENTION

The present invention relates to a method and apparatus for the provision of target data in encrypted form to an accredited professional and to a method and system for recovering the target data in clear; in particular, but not exclusively, the present invention relates to such methods, system and apparatus involving Identifier-Based Encryption.

As used herein, reference to a "professional" is a reference to an individual that has certain recognised skills that the individual uses in carrying out their job. Such skills may range from the skills of a brain surgeon to those of a plumber or the like, without limitation.

BACKGROUND OF THE INVENTION

Professionals working in the same field frequently belong to a professional body one role of which may be to maintain a list of accredited professionals working in the field concerned (though not necessarily members of the body); such a role may, indeed, have regulatory force. Entry on the list of accredited professionals often requires an individual to have obtained certain qualifications but will generally also require that the individual has not committed any major act detrimental to their clients. Thus the accredited status of a professional is not something which once obtained will necessarily continue.

One field where the professional status of an individual is of particular importance is the medical field. This field places high demands not only on the skill of the individuals concerned but also on maintaining the confidentiality of patient records. It is expected that electronic medical records of patients will replace paper records in the near future. The update of these records is likely to be the responsibility of the patient's local doctor (that is, their "general practitioner" or "GP"). The GP, for the purpose of secure preservation of patient data, is likely to use a secure data storage service to store the electronic patient records. In an emergency situation, in which a patient requires medical care, an attending doctor or paramedic (generally, a medical professional) needs to know, as a matter of urgency, the medical history of the patient to prevent giving inappropriate treatments. There is therefore a need for the attending medical professional to obtain the patient's medical records from the data storage service provider; however, this needs to be done in a manner that safeguards the privacy of the records.

Most solutions that have been proposed for dealing with the above situation involve the use of a public key infrastructure (PKI) which would need to be created for the medical professionals. In such a PKI, a professional body for medical professionals would act as a certificate authority providing an accredited medical professional with a certificate confirming their accreditation and public key. In an emergency situation, the medical professional would send a patient identifier together with the professional's own certificate to the patient data storage service. This service would verify the validity of the certificate, encrypt the patient's records with the medical professional's public key, and return the encrypted data to the medical professional.

One disadvantage of the foregoing arrangement is that it does not distinguish between a request from a medical professional carrying out their work in a hospital emergency room and a medical professional who just wants to pry into the details of a patient. Another disadvantage is the need for the data storage service to keep, or have immediate access to, an up-to-date certificate revocation list.

It is an object of the present invention to provide an improved way for professionals to access confidential data in a controlled manner that obviates at least some of the problems associated with prior systems. It is to be understood that the present invention is not limited to the provision of sensitive data to medical professionals but is applicable to all types of professionals.

As will explained hereinafter, the preferred embodiments of the invention utilise Identifier-Based Encryption (IBE) which is an emerging cryptographic schema. For convenience, this known schema will next be described with reference to FIG. 1 of the accompanying drawings. In FIG. 1 a data provider 10 is shown as encrypting payload data 13 using both an encryption key string 14, and public data 15 provided by a trusted authority 12. This public data 15 is related to private data held by the trusted authority; for example, the public data is derived by the trusted authority 12 from private data 17 using a one-way function 18. The data provider 10 then provides the encrypted payload data <13> to a recipient 11 who decrypts it, or has it decrypted, using a decryption key computed by the trusted authority 12 in dependence on the encryption key string and its own private data.

A feature of identifier-based encryption is that because the decryption key is generated from the encryption key string, its generation can be postponed until needed for decryption.

Another feature of identifier-based encryption is that the encryption key string is cryptographically unconstrained and can be any kind of string, that is, any ordered series of bits whether derived from a character string, a serialized image bit map, a digitized sound signal, or any other data source. The string may be made up of more than one component and may be formed by data already subject to upstream processing. In order to avoid cryptographic attacks based on judicious selection of a key string to reveal information about the encryption process, as part of the encryption process the encryption key string is passed through a one-way function (typically some sort of hash function) thereby making it impossible to choose a cryptographically-prejudicial encryption key string. In applications where defence against such attacks is not important, it would be possible to omit this processing of the string.

Frequently, the encryption key string serves to "identify" the intended message recipient and the trusted authority is arranged to provide the decryption key only to this identified intended recipient. This has given rise to the use of the label "identifier-based" or "identity-based" generally for cryptographic methods of the type under discussion. However, depending on the application to which such a cryptographic method is put, the string may serve a different purpose to that of identifying the intended recipient and may be used to convey other information to the trusted authority or, indeed, may be an arbitrary string having no other purpose than to form the basis of the cryptographic processes. Accordingly, the use of the term "identifier-based" or "IBE" herein in relation to cryptographic methods and systems is to be understood simply as implying that the methods and systems are based on the use of a cryptographically unconstrained string whether or not the string serves to identify the intended recipient. Generally, in the present specification, the term "encryption key string" or "EKS" is used rather than "identity string" or "identifier string"; the term "encryption key string" is also used in the shortened form "encryption key" for reasons of brevity.

A number of IBE algorithms are known and FIG. 2 indicates, for three such algorithms, the following features, namely:
- the form of the encryption parameters 5 used, that is, the encryption key string and the public data of the trusted authority (TA);
- the conversion process 6 applied to the encryption key string to prevent attacks based on judicious selection of this string;
- the primary encryption computation 7 effected;
- the form of the encrypted output 8.

The three prior art IBE algorithms to which FIG. 2 relates are:
- Quadratic Residuosity (QR) method as described in the paper: C. Cocks, "An identity based encryption scheme based on quadratic residues", Proceedings of the 8$^{th}$ IMA International Conference on Cryptography and Coding, LNCS 2260, pp 360-363, Springer-Verlag, 2001. A brief description of this form of IBE is given hereinafter.
- Bilinear Mappings p using, for example, a modified Tate pairing t or modified Weil pairing e for which:

$$p: G_1 \times G_1 \to G_2$$

where $G_1$ and $G_2$ denote two algebraic groups of prime order q and $G_2$ is a subgroup of a multiplicative group of a finite field. For the Tate pairing an asymmetric form is also possible:

$$p: G_1 \times G_0 \to G_2$$

where $G_0$ is a further algebraic group the elements of which are not restricted to being of order q. Generally, the elements of the groups $G_0$ and $G_1$ are points on an elliptic curve though this is not necessarily the case. A description of this form of IBE method, using modified Weil pairings is given in the paper: D. Boneh, M. Franklin—"Identity-based Encryption from the Weil Pairing" in *Advances in Cryptology*-CRYPTO 2001, LNCS 2139, pp. 213-229, Springer-Verlag, 2001.
- RSA-Based methods The RSA public key cryptographic method is well known and in its basic form is a two-party method in which a first party generates a public/private key pair and a second party uses the first party's public key to encrypt messages for sending to the first party, the latter then using its private key to decrypt the messages. A variant of the basic RSA method, known as "mediated RSA", requires the involvement of a security mediator in order for a message recipient to be able to decrypt an encrypted message. An IBE method based on mediated RSA is described in the paper "Identity based encryption using mediated RSA", D. Boneh, X. Ding and G. Tsudik, 3rd Workshop on Information Security Application, Jeju Island, Korea, August, 2002.

In all of the above cases, the decryption key is generated by a trusted authority in dependence on the encryption key string.

A more detailed description of the QR method is given below with reference to the entities depicted in FIG. 1 and using the same notation as given for this method in FIG. 2. In the QR method, the trust authority's public data 15 comprises a value N that is a product of two random prime numbers p and q, where the values of p and q are the private data 17 of the trust authority 12. The values of p and q should ideally be in the range of $2^{511}$ and $2^{512}$ and should both satisfy the equation: p,q≡3 mod 4. However, p and q must not have the same value. Also provided is a hash function # which when applied to a string returns a value in the range 0 to N−1.

Each bit of the user's payload data 13 is then encrypted as follows:

The data provider 10 generates random numbers $t_+$ (where $t_+$ is an integer in the range $[0, 2^N]$) until a value of $t_+$ is found that satisfies the equation jacobi($t_+$,N)=m', where m' has a value of −1 or 1 depending on whether the corresponding bit of the user's data is 0 or 1 respectively. (As is well known, the jacobi function is such that where $x^2 \equiv \# \bmod N$ the jacobi (#, N)=−1 if x does not exist, and =1 if x does exist). The data provider 10 then computes the value:

$$s_+ \equiv (t_+ + K/t_+) \bmod N$$

where: $s_+$ corresponds to the encrypted value of the bit m' concerned, and

K=#(encryption key string)

Since K may be non-square, the data provider additionally generates additional random numbers $t_-$ (integers in the range $[0, 2^N)$) until one is found that satisfies the equation jacobi($t_-$, N)=m'. The data provider 10 then computes the value:

$$s_- \equiv (t_- - K/t_-) \bmod N$$

as the encrypted value of the bit m concerned.

The encrypted values $s_+$ and $s_-$ for each bit m' of the user's data are then made available to the intended recipient 11, for example via e-mail or by being placed in a electronic public area; the identity of the trust authority 12 and the encryption key string 14 will generally also be made available in the same way.

The encryption key string 14 is passed to the trust authority 12 by any suitable means; for example, the recipient 11 may pass it to the trust authority or some other route is used—indeed, the trust authority may have initially provided the encryption key string. The trust authority 12 determines the associated private key B by solving the equation:

$$B^2 \equiv K \bmod N \text{ ("positive" solution)}$$

If a value of B does not exist, then there is a value of B that is satisfied by the equation:

$$B^2 \equiv -K \bmod N \text{ ("negative" solution)}$$

As N is a product of two prime numbers p, q it would be extremely difficult for any one to calculate the decryption key B with only knowledge of the encryption key string and N. However, as the trust authority 12 has knowledge of p and q (i.e. two prime numbers) it is relatively straightforward for the trust authority 12 to calculate B.

Any change to the encryption key string 14 will result in a decryption key 16 that will not decrypt the payload data 13 correctly. Therefore, the intended recipient 11 cannot alter the encryption key string before supplying it to the trust authority 12.

The trust authority 12 sends the decryption key to the data recipient 11 along with an indication of whether this is the "positive" or "negative" solution for B.

If the "positive" solution for the decryption key has been provided, the recipient 11 can now recover each bit m' of the payload data 13 using:

$$m' = \text{jacobi}(s_+ + 2B, N)$$

If the "negative" solution for the decryption key B has been provided, the recipient 11 recovers each bit m' using:

$$m' = \text{jacobi}(s_- + 2B, N)$$

SUMMARY OF THE INVENTION

In general terms, the present invention calls for the recovery of encrypted sensitive data to require the involvement not only of a first trusted authority competent in respect of the accreditation of professionals, but also of an organisation engaging the professional and a second trusted authority competent in respect of the accreditation of organisations.

More particularly, according to a first aspect of the present invention, there is provided a method of recovering target data provided in encrypted form to a party as part of a data set with which first and second trusted authorities are associated in a non-subvertible manner, the method comprising:

providing a first element to the party after the first trusted authority has verified that a specific individual is a professional accredited with it;
  providing a second element to the party after both the second trusted authority has verified that a particular organisation is accredited with it, and said particular organisation has verified that said specific individual is engaged by it; and
  the party using both said elements to recover the target data in clear;

at least one of the particular organisation and the first trusted authority ensuring that its verification is for said party as said specific individual before providing the corresponding element.

In one embodiment both the particular organisation and the first trusted authority use the authenticated identity of the party for the specific individual in respect of which they carry out their respective verifications. In another embodiment, the data set identifies said specific individual and one or both of the particular organisation and the first trusted authority check that the authenticated identity of the party corresponds to the specific individual identified in the data set.

Advantageously, the method involves the use of Identifier-Based Encryption (IBE). In one preferred embodiment, the data set comprises a first item encrypted in dependence on encryption parameters comprising a first IBE encryption key string that identifies said specific individual, and public data of the first trusted authority; and a second item encrypted in dependence on encryption parameters comprising a second IBE encryption key string that identifies a specific organisation, and public data of the second trusted authority. In this case, the second trusted authority verifies that the said particular organisation is the specific organisation identified in the second encryption key as well it as being an organisation accredited with the second trusted authority.

The use of the public data of the first and second trusted authorities in encrypting the first and second items provides a non-subvertible link between the data set and the trust authorities as these authorities must be contacted for the corresponding decryption keys. However, it may be noted that the data provider may opt to use the same first and second encryption key strings when encrypting the first and second items of different data sets in which case provision can be made for caching of the corresponding decryption keys, thereby obviating the need for the trusted authorities to be contacted each time target data is provided to the party.

According to a second aspect of the present invention, there is provided a secure data-provision method comprising providing target data from a data provider to a party purporting to be a specific, professionally-accredited, individual engaged by a specific accredited organisation, the target data being provided in encrypted form as part of a data set that comprises:

a first item encrypted, according to an Identifier-Based Encryption, IBE, scheme, in dependence on encryption parameters comprising a first encryption key string that identifies said specific individual, and public data of a first trusted authority competent in respect of professional accreditations; and
  a second item encrypted according to an EBE scheme, in dependence on encryption parameters comprising a second encryption key string that identifies said specific organisation, and public data of a second trusted authority competent in respect of accreditations of organisations;

recovery of the target data in clear requiring decryption of both the first and second items.

According to a third aspect of the present invention, there is provided a system for recovering target data provided in encrypted form to a party as part of a data set with which first and second trusted authorities are associated in a non-subvertible manner, the system comprising:

a first computing entity, associated with the first trusted authority, for providing a first element to the party after verifying that a specific individual is a professional accredited with it;
  a second computing entity associated with the second trusted authority;
  a third computing entity, associated with a particular organisation, for providing a second element to the party after the second computing entity has verified that said particular organisation is accredited with it, and the third computing entity has verified that said specific individual is engaged by it; and
  a fourth computing entity, associated with said party, for decrypting the target data using the first and second elements;

at least one of the first and third computing entities being arranged to ensure that its verification is for said party as said specific individual before providing the corresponding element to the party.

According to a fourth aspect of the present invention, there is provided apparatus for the secure provision of target data to a party purporting to be a specific, professionally-accredited, individual engaged by a specific accredited organisation, the apparatus comprising an encryption subsystem for generating a data set including the target data in encrypted form, the encryption subsystem comprising:

first encryption means for encrypting a first item, according to an Identifier-Based Encryption, IBE, scheme, based on encryption parameters comprising a first encryption key string that identifies said specific individual, and public data of a first trusted authority competent in respect of professional accreditations;
  second encryption means for encrypting a second item, according to an IBE scheme, based on encryption parameters comprising a second encryption key string that identifies said specific organisation, and public data of a second trusted authority competent in respect of accreditations of organisations; and
  means for forming the data set using at least the encrypted first and second items;

the recovery of the target data in clear requiring decryption of both the first and second items.

The present invention also envisages user computing devices for use by professionals in recovering encrypted target data.

BRIEF DESCRIPTION OF THE DRAWINGS

Embodiments of the invention will now be described, by way of non-limiting example, with reference to the accompanying diagrammatic drawings, in which.

BEST MODE OF CARRYING OUT THE INVENTION

The embodiments of the invention to be described hereinafter are all placed in a medical context with a requesting party only being able to obtain access to a patient record if the party is a medical professional (for example, a doctor or paramedic) accredited with a medical professional trusted authority and engaged by a medical organisation (such as a hospital) accredited with a medical organisation trusted authority. However, it is to be understood that these embodiments can also be applied in other fields beyond the medical world.

Figure 3:
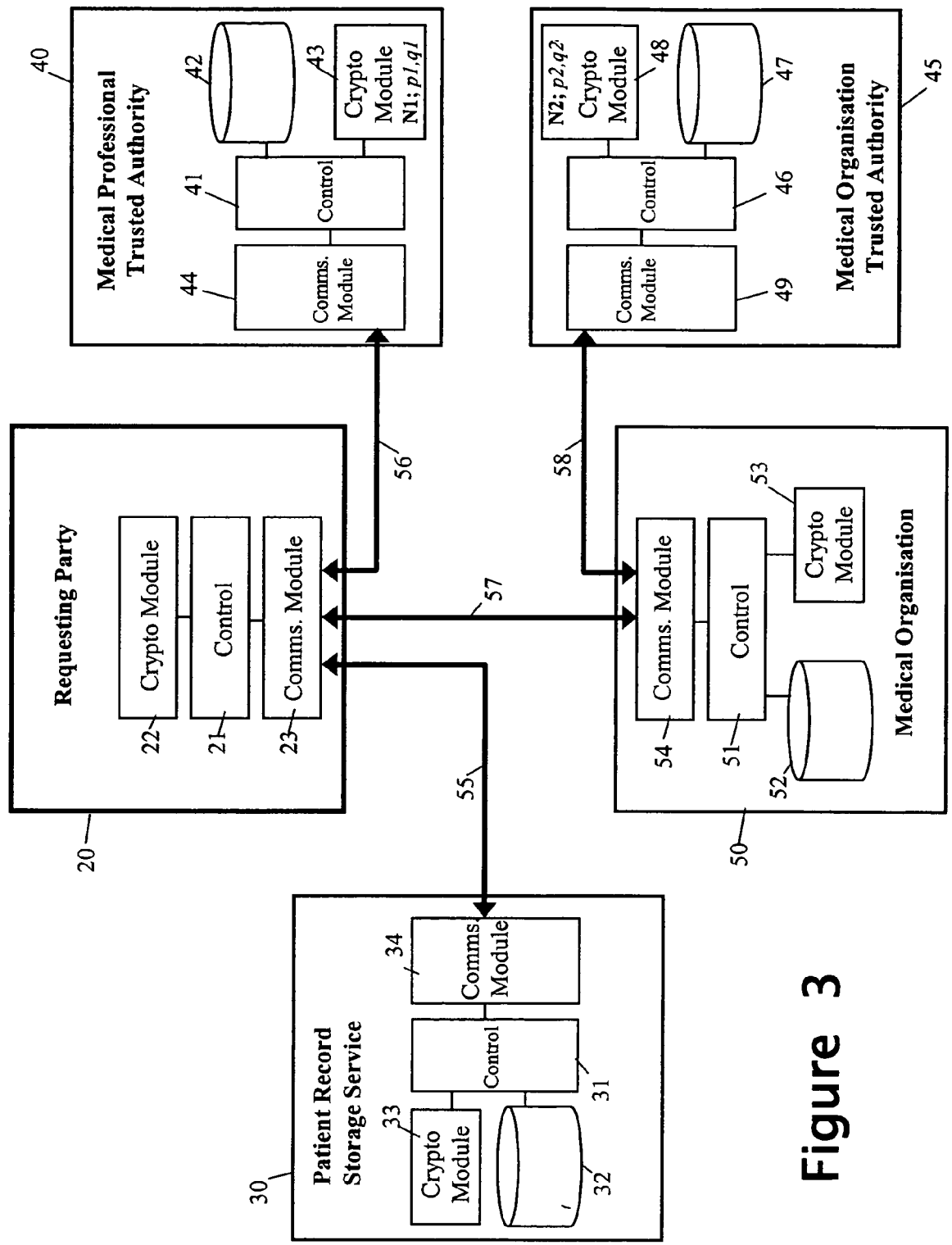
FIG. 3 is a diagram showing the general arrangement of entities involved in the embodiments described with respect to FIGS. 3 to 8.

FIG. 3 illustrates the general arrangement of the entities involved in all the embodiments described below. More particularly, this arrangement comprises a first computing entity 20 (such as a personal digital assistant) associated with a requesting party wishing to receive a patient record; a second computing entity 30 associated with a patient record storage service; a third computing entity 40 associated with a medical professional trusted authority competent in respect of the accreditation of medical professionals (that is, trusted as authoritative concerning the accreditation of such professionals); a fourth computing entity 45 associated with a medical organisation trusted authority competent in respect of the accreditation of medical organisations; and a fifth computing entity 40 associated with a particular medical organisation. The computing entities 20, 30, 40, 45 and 50 are typically based around general-purpose processors executing stored programs. The computing entities 20, 30, 40, 45 and 50 intercommunicate as needed (see arrows 55-58) via, for example, the internet or other network though it is also possible that at least some of the entities actually reside on the same computing platform. As will be described below, at least certain of the inter-entity communications are arranged to take place securely with the communicating parties authenticating each other; to this end, the entities are equipped with suitable communication modules well understood by persons skilled in the art.

In the following, references to the requesting party, patient record storage service, the medical professional trusted authority, the medical organisation trusted authority, and the medical organisation are generally used interchangeably with references to their respective computing entities 20, 30, 40, 45 and 50. Furthermore, for convenience the terms "patient record storage service" and "trusted authority" are abbreviated to "PRSS" and "TA" respectively.

In functional terms, the requesting-party entity 20 comprises a communications module 23 for communicating with the entities 30, 40 and 50, a control module 21 for controlling the general operation of the entity 20 and for providing a user interface and at least short-term storage, and a cryptographic module 22 for executing certain cryptographic functions that vary between the embodiments to be described below.

The PRSS entity 30 comprises a communications module 34 for communicating with the requesting party entity 20 (and possibly also with the entities 40 and 45), a control module 31 for controlling the general operation of the entity 30, a database 32 for holding patient records, and a cryptographic module 33 for executing certain cryptographic functions that also vary between the embodiments to be described below.

The medical professional TA entity 40 comprises a communications module 44 for communicating with the requesting party entity 20 (and possibly also with the entity 30), a control module 41 for controlling the general operation of the entity 40, a database 42 for holding medical professional accreditation data, and a cryptographic module 43 for executing certain cryptographic functions.

The medical organisation TA entity 45 comprises a communications module 49 for communicating with the medical organisation entity 50 (and possibly also with the entity 30), a control module 46 for controlling the general operation of the entity 45, a database 47 for holding medical organisation accreditation data, and a cryptographic module 48 for executing certain cryptographic functions.

The medical organisation entity 50 comprises a communications module 54 for communicating with the requesting party entity 20 and the medical organisation TA 45, a control module 51 for controlling the general operation of the entity 50, a database 52 for holding data about medical professionals engaged by the organisation including their data access authorisation levels (in particular, whether they are authorised to access patient records), and a cryptographic module 53 for executing certain cryptographic functions.

The specific embodiments now to be described all employ Identifier-Based Cryptography (in the present case, the QR IBC method) to enable the PRSS entity 30 to specify conditions to be met by parties wishing to access patient records provided by the entity 30.

More particularly, the TAs 40 and 45 have respective IBE public data N1 and N2 and corresponding respective IBE private data p1,q1 and p2,q2 used in forming their public data. The PRSS entity 30 knows the public data N1 and N2 of the two TAs (for example, as a result of the latter each publishing its public data in a certificate digitally signed using a locally-held private key of a public/private key pair associated with the trusted authority).

When the requesting party 20 wants to access a patient record, it makes a request (arrow 55) to the PRSS entity 30 in which it not only identifies the patient concerned, but also identifies both itself (by name or, preferably, by another identifier such as a public key of an asymmetric public/private key pair the private key of which is held by the party 20), and the medical organisation for which the party 20 is currently working (again, either by name or by another identifier such as the public key of an asymmetric public/private key pair the private key of which is held by the organisation).

The PRSS entity 30 responds to the request by the party 20 by encrypting the requested patient record (referred to herein as the "target record" or, more generally, the "target data") and providing it (arrow 55) to the party 20 as part of a data set that comprises encrypted first and second items. The first data-set item is IBE encrypted using the party's supplied identity as an IBE encryption key and the public data N1 of the medical professional TA 40. The second data-set item is IBE encrypted using the supplied organisation identity as an IBE encryption key and the public data N2 of the medical organisation TA 45. To recover the target patient record in clear, it is necessary to decrypt both the first data-set item and the second data-set item and this requires a first IBE decryption key provided by the medical professional TA 40 and a second decryption key provided by the medical organisation TA 45.

As will become apparent hereinafter, the composition of the data set of which the encrypted target patient record forms a part varies from embodiment to embodiment as does the relationship between the first and second data-set items and the target patient record (indeed, in one embodiment, the first data-set item is the target patient record).

The party entity 20 on receiving the data set including the encrypted target record, seeks to obtain the first decryption key from the medical professional TA 40 and in doing so provides the related encryption key to the TA 40. The TA 40 only returns the decryption key if it is satisfied that the individual identified in the encryption key is a professional accredited with it as indicated by the data it holds in its database 42; the TA 40 may also require the party to prove that they are this identified individual. In certain embodiments, the TA 40 may be arranged to receive, decrypt and return the first data-set item rather than providing the first decryption key to the party 20.

The party entity 20 also requests (arrow 57) the second decryption key from the medical organisation entity 50, providing the latter with the encryption key that identifies the organisation indicated to the PRSS entity by the party 20. The organisation 50, either before or after carrying out certain checks to be described, asks (arrow 58) the medical organisation TA 45 to provide the second decryption key on the basis of the supplied encryption key. The TA 45 only supplies the requested key if it is satisfied that the requesting organisation is the same organisation as identified in the encryption key and that the organisation is accredited with it according to the data held in the database 47. Assuming that the TA 45 provides the second decryption key to the organisation 50, and provided this entity 50 is satisfied that the party 20 (or, in certain embodiments, the individual identified by the party to the PRSS entity 30), is engaged by the organisation with appropriate data access authority as indicated by data in the database 52, the organisation returns (arrow 57) the second decryption key, or the second data-set item decrypted using this key, to the party 20.

The final recovery of the target patient record takes place at the party entity 20. This recovery is only possible if the party 20 is a medical professional accredited with the medical professional TA 40 and is engaged by a medical organisation accredited with the medical organisation TA 45. However, it may be noted that the PRSS entity 30 may use the same encryption keys when encrypting the first and second items of data sets associated with different record requests by the party 20; in this case, the corresponding decryption keys may be cached by the entities that carry out IBE decryption, thereby obviating the need for the TAs 40, 45 to be contacted each time a target record is provided to the party 20.

Figure 1:
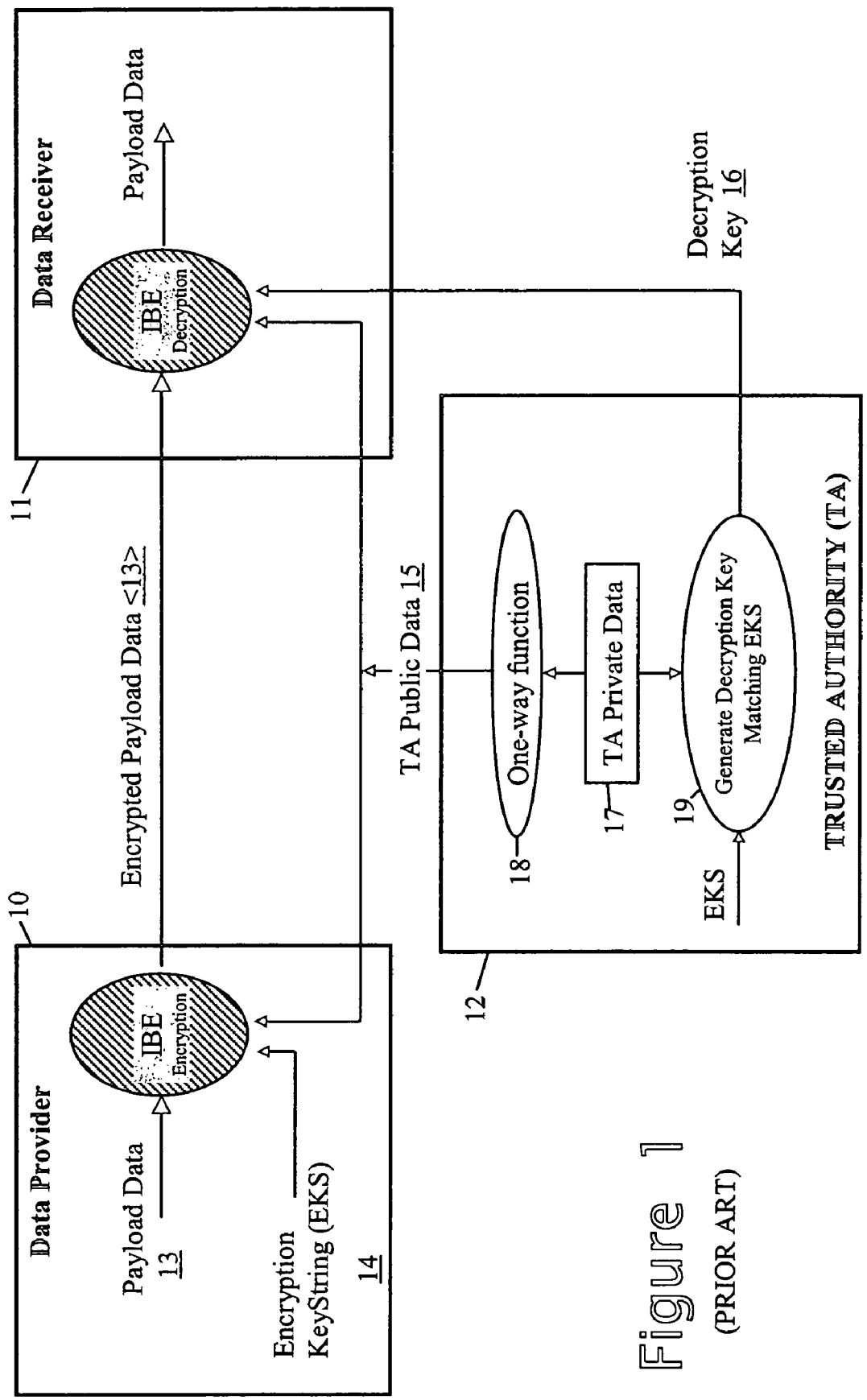
FIG. 1 is a diagram illustrating the operation of a prior art encryption schema known as Identifier-Based Encryption, IBE.
Figure 2:
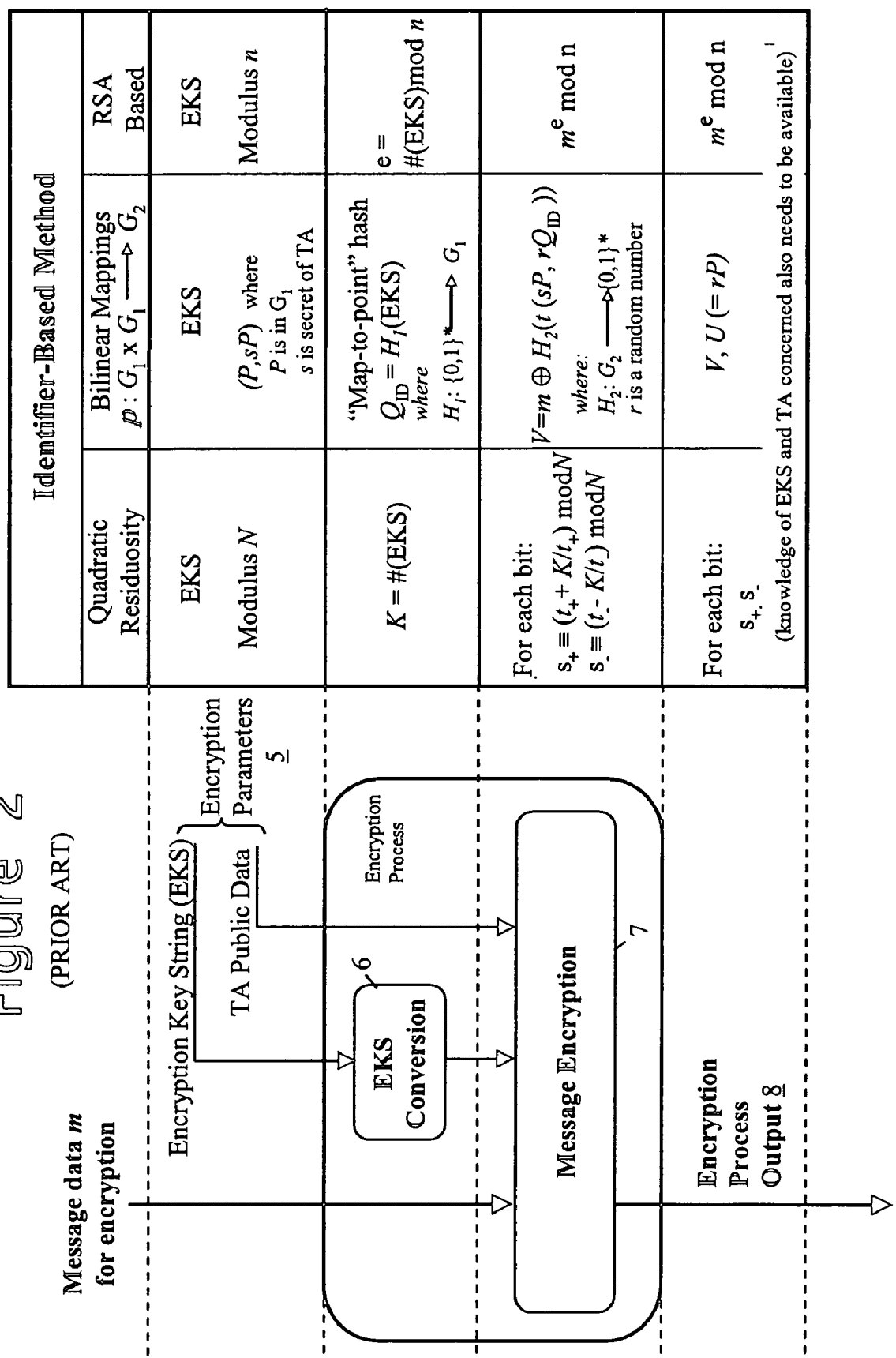
FIG. 2 is a diagram illustrating how certain IBE operations are implemented by three different prior art IBE methods.

So far as the IBE cryptographic processes are concerned, the correspondence between the entities of FIG. 3 and those of FIG. 1 will be apparent to persons skilled in the art.

Specific IBE-based embodiments will now be described with reference to FIGS. 3 to 8. In these Figures, the PRSS entity 30 and the initial request from the party entity to the PRSS entity are not depicted and consideration of these embodiments starts with the data set returned by the PRSS entity 30, it being appreciated that this data set has been generated by the functional elements 31 and 33 of the entity 30 using the data supplied to it in the initial request, the TA public data N1 and N2, and the patient record extracted from the database 32.

Figure 4:
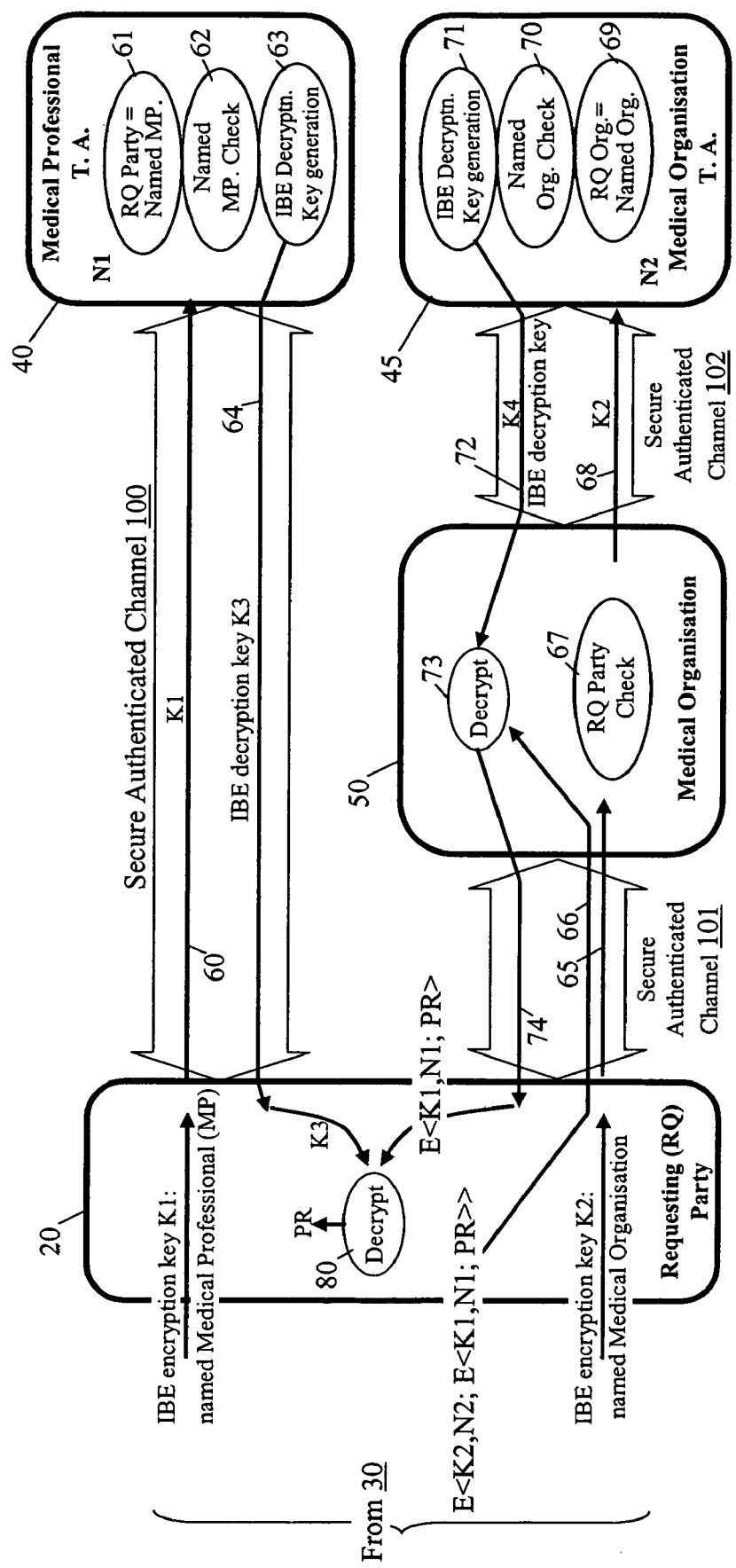
FIG. 4 is a diagram of a first specific embodiment of the present invention.

Considering first the FIG. 4 embodiment, the data set returned by the PRSS entity 30 comprises:
 a first IBE encryption key K1 comprising an identification of an individual (the party 20) purporting to be a medical professional (MP);
 a second IBE encryption key K2 comprising an identification of an organization purported by the party 20 as being an accredited medical organization ("MO") by which the party is engaged;
 an encrypted first item formed by the IBE encryption of the target patient record "PR" using the first encryption key K1 and the public data N1 of the medical professional TA 40—this is represented by the expression E<K1,N1; PR> where E<> denotes that the element appearing in the brackets after the semi colon has been encrypted using the element or elements appearing before the semi colon;
 an encrypted second item formed by the IBE encryption of the first item using the second encryption key K2 and the public data N2 of the medical organization TA 45—this is represented by the expression E<K2,N2; E<K1,N2; PR>>.

It will be appreciated that the encrypted first item (that is, the second item) does not appear explicitly in the data set but only in its further encrypted form as the encrypted second item.

The entity 20 now establishes a secure authenticated communication channel 100 with the medical professional TA 40 and requests (arrow 60) the IBE decryption key K3 corresponding to IBE encryption key K1, this latter being passed in the request to the entity 40. The entity 40 first checks (process 61) that the requesting party, as established by authentication when setting up channel 100, is the same as the medical professional (MP) identified in the encryption key K1. If this check is passed, the entity 40 then checks (process 62) that the party/MP is accredited as a medical professional with the entity 40. The checks 61 and 62 can, in fact, be carried out simultaneously or in reverse order. Only if both these checks are passed does the entity 40 proceed with the generation (process 63) of the decryption key K3 by using the encryption key K1 and the private data p1,q1 of the entity 40. The decryption key K3 is then returned (arrow 64) over the channel 100 to the party entity 20. The key K3 could have been generated in advance of, or in parallel with, the checks 61 and 62 being carried out—what is important is that the key K3 is not returned until the checks have been passed.

The entity 20 also establishes a secure authenticated communication channel 101 with the medical organization entity 50 and passes it both the IBE encryption key K2 (arrow 65) and the encrypted second item (arrow 66). The entity 50 first checks (process 67) that the party 20, authenticated during set up of the channel 101, is an individual engaged by it with authority to access patient records. "Engaged" can either be taken as currently engaged over a sustained period (for example, of weeks, months, years or for an unspecified duration), or be taken to be actually on duty for the organization at the current instance. The entity 50 may (or may not) also check that it is the organization identified in the encryption key K2. If the or each of these checks is passed, the medical organization entity 50 sets up a secure authenticated communication channel 102 with the medical organization TA entity 45 and passes it (arrow 68) the encryption key K2 with a request for the corresponding decryption key K4.

The TA entity 45 first checks (process 69) that the requesting organization, as authenticated during set up of channel 102, is the organization identified in the encryption key K2. If this check is passed, the entity 45 then checks (process 70) that the organisation is accredited as a medical organisation with the entity 45. The checks 69 and 70 can be carried out simultaneously or in reverse order. Only if both these checks are passed does the entity 45 proceed with the generation (process 71) of the decryption key K4 by using the encryption key K2 and the private data p2,q2 of the entity 45. The decryption key K4 is then returned (arrow 72) over the channel 102 to the medical organisation entity 50. The key K4 could have been generated in advance of, or in parallel with, the checks 69 and 70 being carried out—what is important is that the key K4 is not returned until the checks have been passed.

On receiving the decryption key K4, the medical organisation entity 50 uses it to decrypt (process 73) the encrypted second item. The second item E<K1,N1; PR> is then passed back (arrow 74) over the secure channel 101 to the party entity 20.

The party entity 20 finally recovers the target patient record in clear by using the decryption key K3 to decrypt the second item (process 80).

Figure 5:
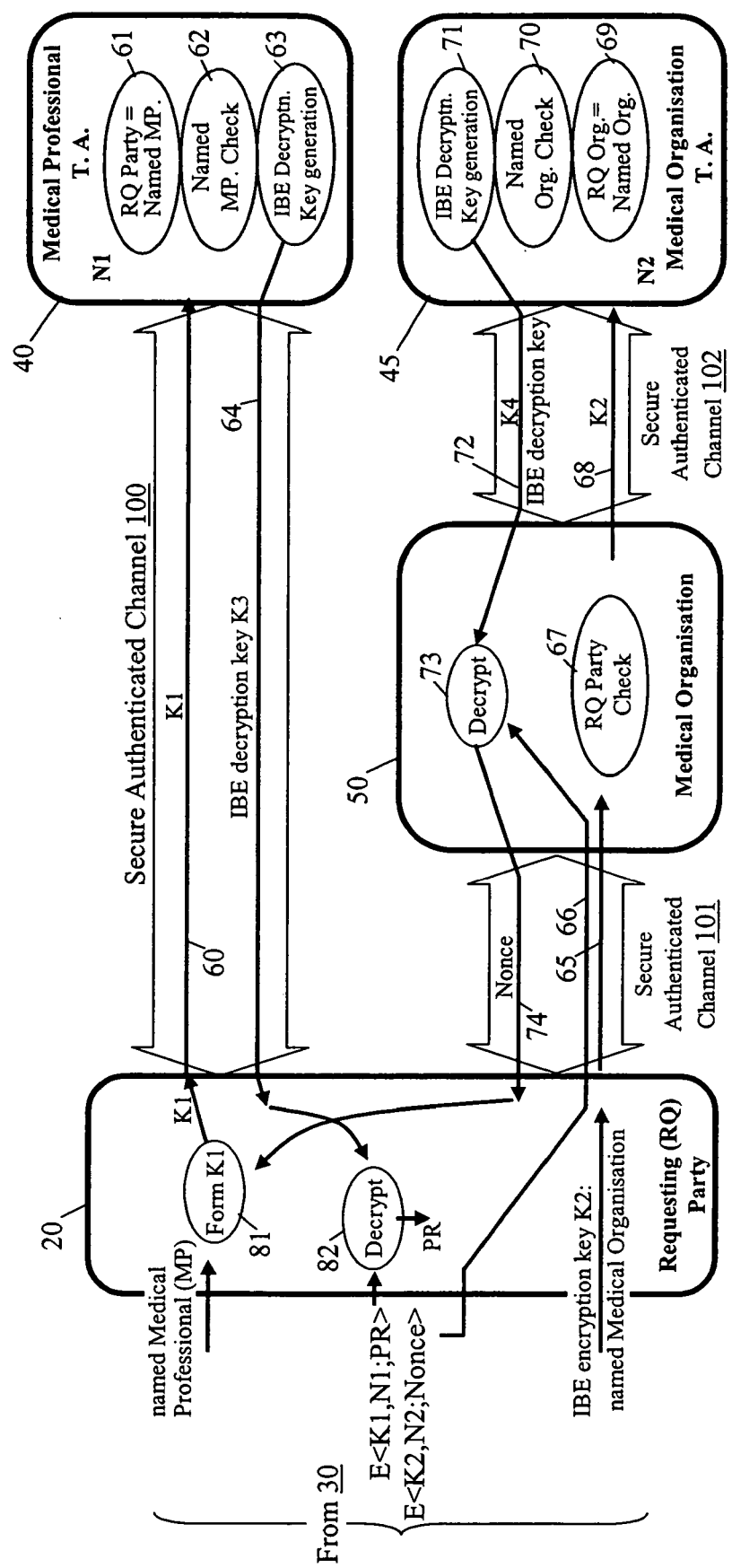
FIG. 5 is a diagram of a second specific embodiment of the present invention.
Figure 6:
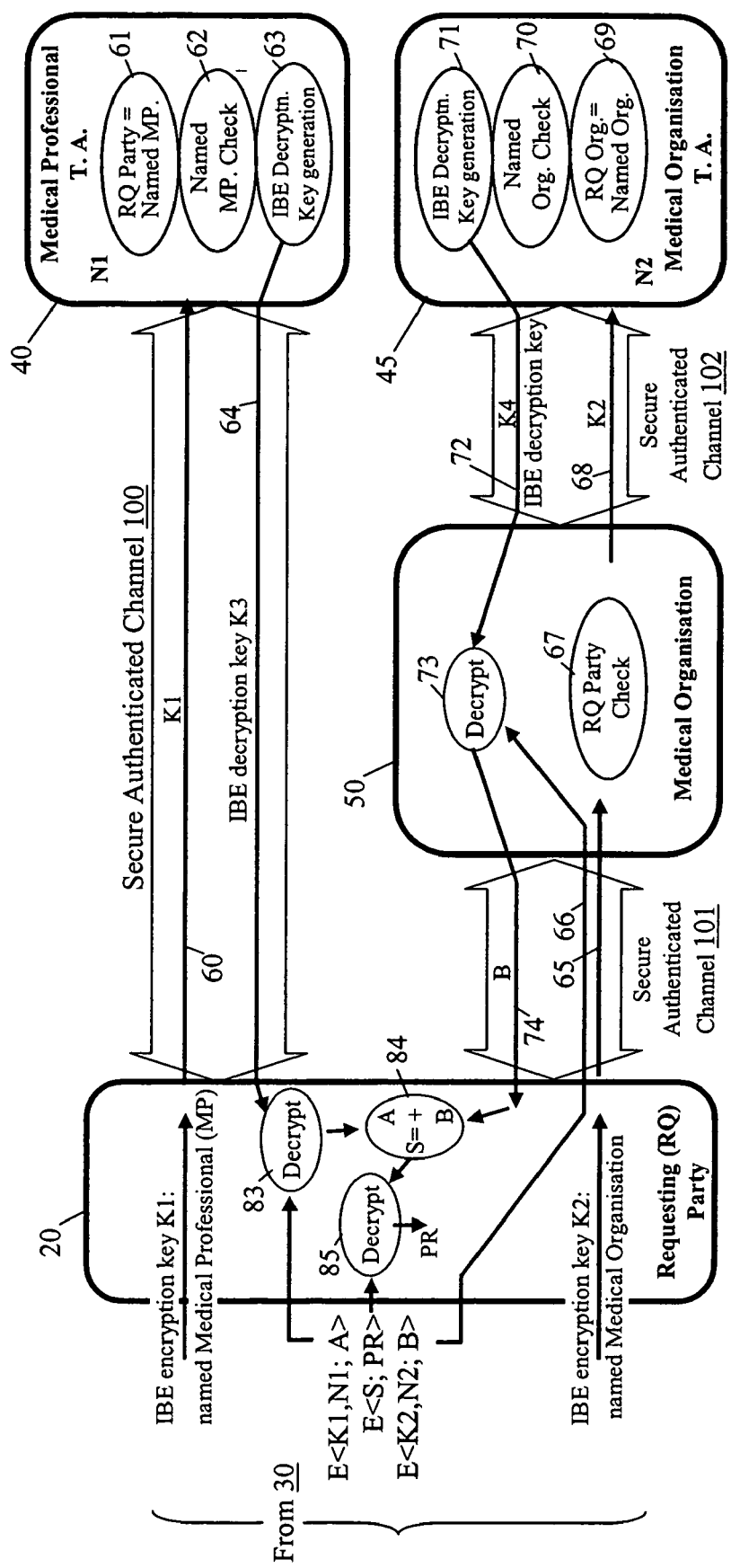
FIG. 6 is a diagram of a third specific embodiment of the present invention.

In the embodiments of FIGS. 4, 5 and 6 to be described below, the roles of the two TA entities 40 and 45 and of the medical organisation entity 50 are substantially the same as for the FIG. 4 embodiment, namely:

the medical professional TA entity 40, after carrying out checks 61 and 62, provides the party entity 20 with an IBE decryption key K2 for decrypting a first item encrypted with a first IBE encryption key K1, the medical organisation TA entity 45, after carrying out checks 69 and 70, provides the medical organisation entity 20 with an IBE decryption key K4 for decrypting a second item encrypted with a second IBE encryption key K2, and the medical organisation entity 50, after carrying out check 67, decrypts the second item using the key K4 and returns the decrypted second item to the party entity 20.

The differences between the embodiments of FIGS. 3 to 6 lie in the contents of the data sets provided by the PRSS entity 30 and how these contents are used to recover the target patient record in clear.

Considering next the embodiment of FIG. 5, in this embodiment the data set provided by the PRSS entity 30 comprises:

identification of an individual (the party 20) purporting to be a medical professional (MP), this identification being that used by the PRSS entity 30, in combination with a nonce (random number), for a first IBE encryption key K1;

a second IBE encryption key K2 comprising an identification of an organization purported by the party 20 as being an accredited medical organization ("MO") by which the party is engaged;

an encrypted first item E<K1,N1;PR> formed by the IBE encryption of the target patient data record "PR" using the first encryption key K1 and the public data N1 of the medical professional TA 40;

an encrypted second item E<K2,N2; Nonce> formed by the IBE encryption of the nonce used in the first encryption key K1, using the second encryption key K2 and the public data N2 of the medical organization TA 45.

In this embodiment, the party entity 20 first obtains the decrypted second item (the nonce used in the encryption key K1) from the medical organisation entity 50 and then uses this nonce, together with the medical professional identifier provided by the PRSS entity 30, to re-form (process 81) the encryption key K1. The re-formed key K1 is passed to the entity 40 to obtain the corresponding decryption key K3 which is then used to decrypt (process 82) the encrypted first item and recover the target patient record in clear.

Considering the embodiment of FIG. 6, in this embodiment the data set provided by the PRSS entity 30 comprises:

a first IBE encryption key K1 comprising identification of an individual (the party 20) purporting to be a medical professional (MP);

a second IBE encryption key K2 comprising an identification of an organization purported by the party 20 as being an accredited medical organization ("MO") by which the party is engaged;

the target patient record encrypted using a symmetric key S;

an encrypted first item E<K1,N1;A> formed by the IBE encryption of a first part A of the symmetric key S using the first encryption key K1 and the public data N1 of the medical professional TA 40;

an encrypted second item E<K2,N2; B> formed by the IBE encryption of a second part B of the symmetric key S using the second encryption key K2 and the public data N2 of the medical organization TA 45.

In this embodiment, the party entity 20 obtains the decryption key K3 from the medical professional TA entity 40 and uses it to decrypt (process 83) the encrypted first item to provide the first part A of the symmetric key S. The entity 20 also obtains the decrypted second item (the second part B of the symmetric key S) from the medical organisation entity 50. The party entity 20 then combines A and B (process 84) to re-form the symmetric key S which it thereafter uses to decrypt the target patient record (process 85).

Rather than the symmetric key S being simply split into two parts A and B and re-formed by concatenation of A and B, a more complex relationship between S, A and B is preferred that avoids disclosure of A or B providing any information about S. By way of example, A and B could be created first and then S derived as a hash of A and B, i.e. S=Hash(A,B). An alternative approach would be to use Shamir's security sharing.

Figure 7:
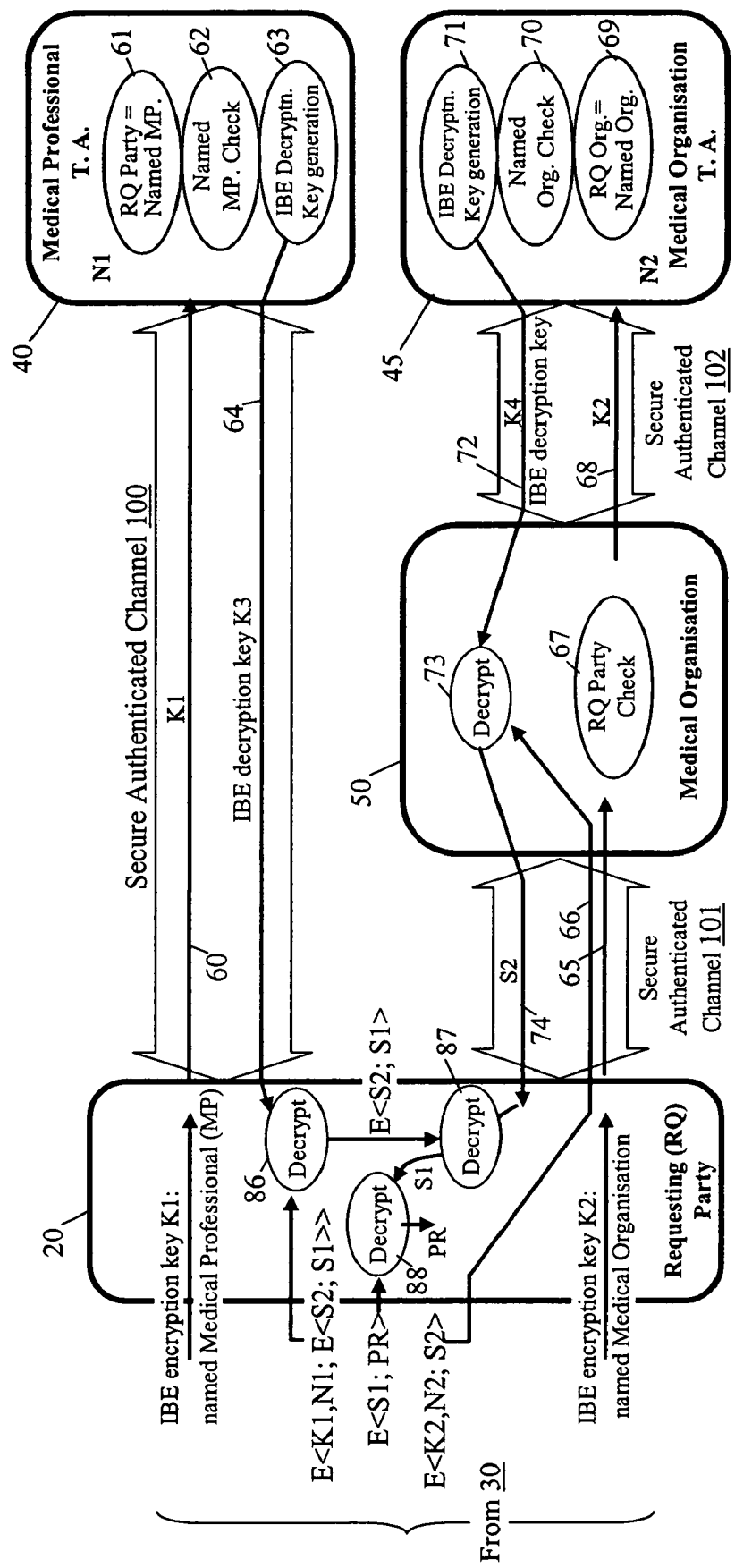
FIG. 7 is a diagram of a fourth specific embodiment of the present invention.

Considering the embodiment of FIG. 7, in this embodiment the data set provided by the PRSS entity 30 comprises:

a first IBE encryption key K1 comprising identification of an individual (the party 20) purporting to be a medical professional (MP);

a second IBE encryption key K2 comprising an identification of an organization purported by the party 20 as being an accredited medical organization ("MO") by which the party is engaged;

the target patient record encrypted using a first symmetric key S1;

an encrypted first item E<K1,N1;E<S2;S1>> formed by the IBE encryption of a component using the first encryption key K1 and the public data N1 of the medical professional TA 40, the component concerned being the first symmetric key S1 encrypted using a second symmetric key S2;

an encrypted second item E<K2,N2; S2> formed by the IBE encryption of the second symmetric key S2 using the second encryption key K2 and the public data N2 of the medical organization TA 45.

In this embodiment, the party entity 20 obtains the decryption key K3 from the medical professional TA entity 40 and uses it to decrypt (process 86) the encrypted first item to provide the component E<S2; S1>. The entity 20 also obtains the decrypted second item (the second symmetric key S2) from the medical organisation entity 50 which it then uses to decrypt (process 87) the component E<S2; S1> and obtain the first symmetric key S1. The party entity 20 then uses the first symmetric key S1 to decrypt the encrypted target patient record (process 88).

It will be appreciated that the data set provided by the PRSS entity 20 may take many other forms without affecting the roles played by the entities 40, 45 and 50. Other variants that modify the operation of the entities 40, 45 and 50 are also possible. For example, in the embodiments of FIGS. 3 to 6 if the PRSS entity 30 is arranged to use the same first encryption key K1 when encrypting the first items of successive data sets provided to the same party (that is, data sets provided in response to successive patient record requests from the party 20), it is possible to arrange for the corresponding decryption key K3 to be cached by the entity 20 when first obtained from the TA entity 40 for use in decrypting the first item of the first of these data sets, and then have the entity 20 re-use this key K3 from cache for the other data sets that have their first items encrypted with same encryption key as the first item for which the decryption key was obtained. In a similar manner, if the PRSS entity 30 uses the same encryption key K2 for encrypting the second items of successive data sets, the medical organisation entity 50 can cache the corresponding decryption key K4 when first obtained from the TA entity 45 and subsequently use the key from cache. Of course, re-use of either decryption key from cache means that the checks carried out by the corresponding TA entity are avoided; it is therefore preferable for the PRSS entity 30 to limit either the number of times or the period over which it re-uses the same encryption key; for example, the PRSS entity 30 maybe arranged to change the first encryption key K1 once a month and to change the second encryption key K3 daily. Changing an encryption key whilst retaining the identification of the medical professional or medical organisation identified in the key is readily done by including a fresh nonce each time the key is to be changed; every time a new nonce is included in an encryption, the corresponding TA entity 40, 45 must be involved to generate the corresponding decryption key thereby resulting in the checks associated with the TA entity to be effected. Of course, the encryption keys K1 and K2 could be changed at every usage; however, this may not be desirable where speed of retrieval of a patient record is important as in emergency medical situations.

Another variant generally applicable to all the embodiments of FIGS. 3 to 6 is for the TA entity 45, rather than passing the decryption key K3 to the party entity 20, to use this key itself to decrypt the encrypted first item and then provide the first item back to the party entity 20. Similarly, the TA entity 45, rather than passing the decryption key K4 to the organisation entity 50, can use this key itself to decrypt the encrypted second item and then provide the second item back to the organisation entity 20. It is also possible to arrange for the medical organisation entity 50 to pass back to the party entity 20 the element it receives from the TA entity 45, whether this be the decryption key K4 or the recovered second element, without using the element itself. These variants are not, however, preferred and in any event the final decryption of the patient record should normally be restricted to being done at the party entity 20.

Figure 8:
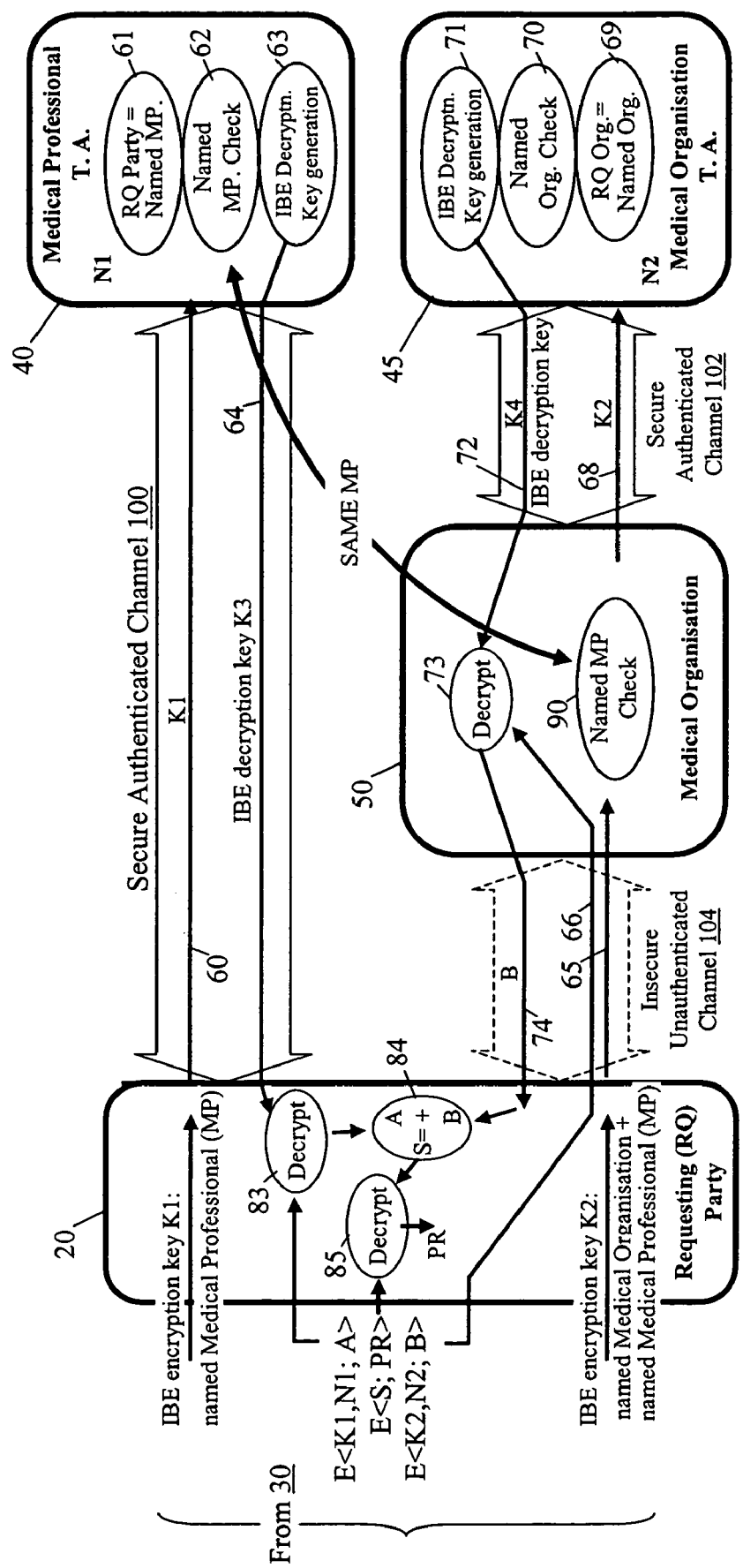
FIG. 8 is a diagram of a first variant of the FIG. 6 embodiment.

FIG. 8 shows a further variant here applied to the FIG. 6 embodiment but also applicable to the embodiments of FIGS. 3, 4 and 6. In the FIG. 8 variant the second encryption key K2 comprises not only identification of a medical organisation, but also the identification of a medical professional contained in the first encryption key K1. This enables the medical organisation entity 50 to check (process 90) that the medical professional checked out by the medical professional TA entity 45 is also engaged by the organisation 50 with authority to access patient records. Whilst the medical organisation entity 50 preferably also checks that the party with which it is communicating is the medical professional identified in the second encryption key, this is not essential because the medical organisation can be sure that only the medical professional identified in the encryption keys will be able to receive the first decryption key K3 from the medical professional TA entity 40. The role of the medical organisation 50 is thus simply to provide the key K4 if the medical professional identified in the first encryption key to the medical professional TA entity 40 is engaged by an organisation accredited with the medical organisation entity 45. Indeed, provision of the key K4 to the party 20 can be done over an insecure, unauthenticated, channel 104 as the key K4 will only be of value to a party that also possesses the first decryption key K3; provision over a secure channel is, however, preferred.

Figure 9:
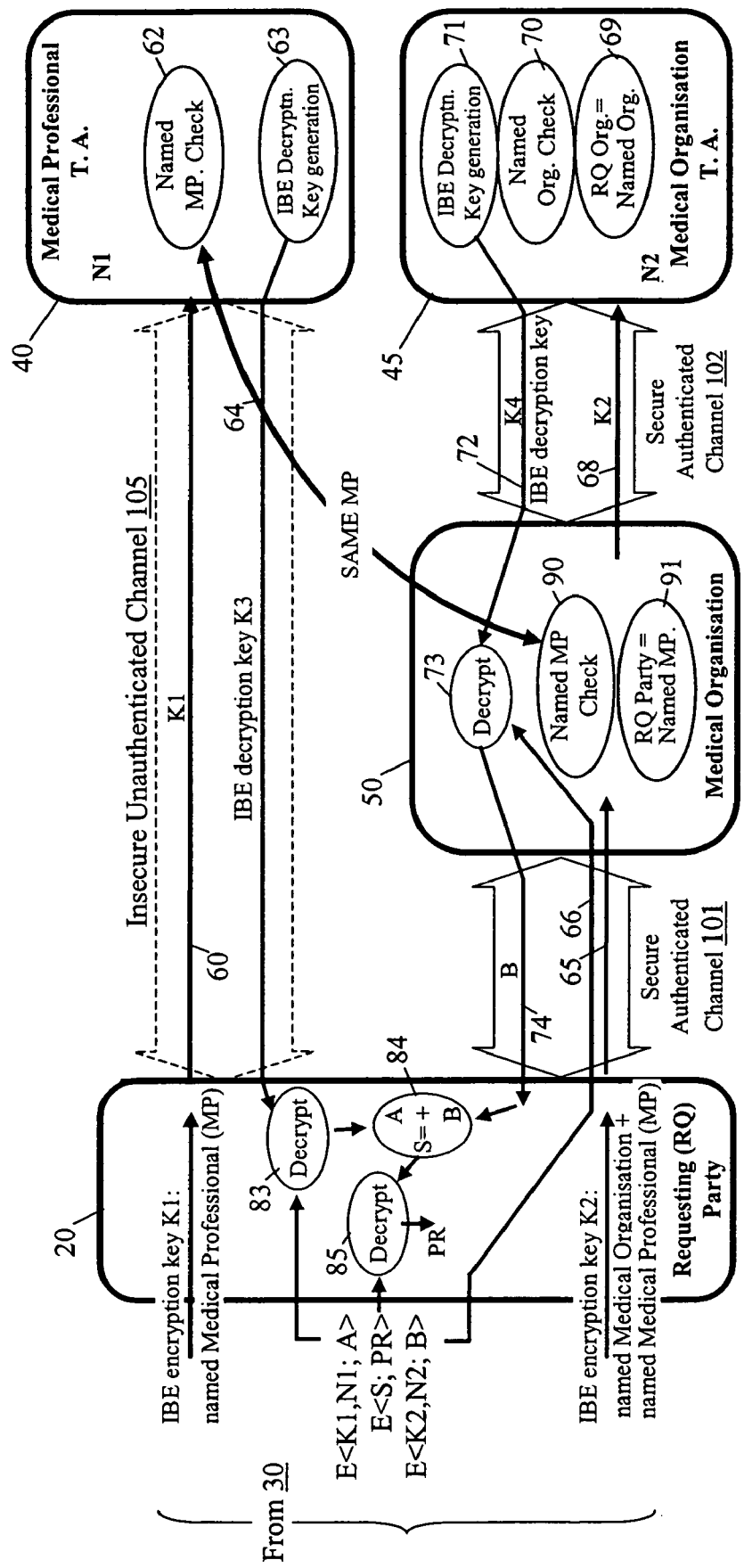
FIG. 9 is a diagram of a second variant of the FIG. 6 embodiment.

FIG. 9 illustrates another variant applied to the FIG. 6 embodiment but also applicable to the embodiments of FIGS. 3, 4 and 6. The FIG. 9 variant, like that of FIG. 8, is based on the second encryption key including not only identification of a medical organisation, but also identification of the same medical professional as identified in the first encryption key. In this variant, the medical organisation entity 50 both checks that the party 20 is the medical professional identified in the second encryption key K2 (process 91) and checks that this professional is engaged by the organisation 50 with authority to access patient records (process 90). Since the decrypted second item will only be available to the party who is the medical professional identified in the encryption keys, the medical professional TA entity 40 need only check that the professional identified in the first encryption key K1 is accredited with it and return the first decryption key K3 to the requesting party; the TA entity 40 need neither check that the party 20 is the identified medical professional nor provide the key K3 in a secure manner (in FIG. 9 the entities 20 and 40 are depicted as communicating via an insecure, unauthenticated, channel 105). Of course, in reality communication between the entities 20 and 40 is preferably by a secure channel and the entity 40 preferably does check that the party 20 is the professional identified in the first encryption key.

It will also be appreciated that many other variants are possible to the above described embodiments of the invention. For example, the data set provided by the PRSS entity 30 need not all be provided to the party 20 but components of it could be passed to the entities 40 and 50 directly for their use. Similarly, since the party entity 20 may well be connected to a network run by the medical organisation 50, the latter can be arranged to intercept the data set and copy or strip out the components it needs before passing on the data set, or the remainder of it, to the party 20.

In the above-described embodiments, no restrictions have been placed on the professional or organisation identified by the party to the PRSS entity 30 when requesting a patient record. However, the PRSS entity 30 can be arranged to authenticate the party 30 and use the authenticated identity of the party in the first encryption key K1. Furthermore, the party entity 20 can take the form of a trusted computing platform provided by the organisation 50 and adapted to reliably provide the PRSS entity 30 with the identifications of both the party 20 and the organisation 50. One suitable form of trusted platform is specified in "TCPA—Trusted Computing Platform Alliance Main Specification v1 .1" www.trustedcomputing.org, 2001 and described in the book "trusted computing platforms —tcpa technology in context"; Pearson (editor); Prentice Hall; ISBN 0-13-009220-7". The computing entity 50 is, preferably, also a trusted computing platform the status of which is verifiable by the TA entity 45.

Where the identification of the professional and organisation to the PRSS entity 30 is not controlled or checked, then there may be little to be gained by using these identifications in the IBE encryption keys in which case the checks carried out by the entities 40, 45 and 50 are simply that the party 20 itself is a medical professional accredited with the medical professional TA entity 40 and engaged by an organisation 50 which is accredited with the medical organisation TA entity 45.

The present invention is not limited to the QR IBE method used in the above-described embodiments and other IBE cryptographic methods can be used such as IBE methods that make use of Weil or Tate pairings, or are RSA based.

Furthermore, embodiments of the invention based on cryptographic techniques other than IBE are also possible. For example, in variant of the FIG. 6 embodiment, the PRSS entity 30 encrypts the quantity A and an identifier of a medical professional using a public key of a first public/private asymmetric key pair the private key of which is held by the medical professional TA entity 40. Similarly, the PRSS entity 30 also encrypts the quantity B and an identifier of a medical organisation using a public key of a second public/private asymmetric key pair the private key of which is held by the medical organisation TA entity 45. In this case, the TA entities 40 and 45 first use their respective private keys to decrypt the data encrypted using their public keys, and then carry out their checks 61,62; 69,70 as described above for the FIG. 6 embodiment before passing the quantities A and B respectively to the party 20 and the medical organisation 50. The organisation 50 passes on the quantity B to the party 20 after carrying out its check 67.

The variants discussed above in relation to the IBE embodiments (including, in particular, those of FIGS. 7 and 8) are generally also applicable to the non-IBE embodiments; for example, the encrypted data provided to the TA entities in the example described in the foregoing paragraph need not include identifications of a medical professional or medical organisation.

The invention claimed is:

1. A secure data-provision method for providing target data from a data provider to a party purporting to be a specific, professionally-accredited, individual engaged by a specific accredited organization, the target data being provided in encrypted form as part of a data set; the method comprising:
encrypting a first item, by a processor executing an Identifier-Based Encryption, IBE, scheme, in dependence on encryption parameters comprising a first encryption key string that identifies said specific individual, and public data of a first trusted authority competent in respect of professional accreditations; and
encrypting a second item, by a processor executing an IBE scheme, in dependence on encryption parameters comprising a second encryption key string that identifies said specific organization, and public data of a second trusted authority competent in respect of accreditations of organizations; and
forming said data set using at least the encrypted first and second items;
recovery of the target data in clear requiring decryption of both the first and second items.

2. The method according to claim 1, wherein the first item comprises the target data, and the second item comprises the encrypted first item.

3. The method according to claim 1, wherein the first item comprises the target data, and the second item comprises a nonce; the first encryption key string comprising, in combination, an identifier of said specific individual and said nonce.

4. The method according to claim 1, wherein the first item comprises first data, and the second item comprises second data; the data set further comprising said target data encrypted using a symmetric key that can be formed by using both said first and second data.

5. The method according to claim 1, wherein the data set comprises, in addition to said first and second items, said target data encrypted using a first symmetric key, the second item comprising a second symmetric key, and the first item comprising the first symmetric key encrypted using the second symmetric key.

6. A secure data-provision method for providing target data from a data provider to a party purporting to be a specific, professionally-accredited, individual engaged by a specific accredited organization, the target data being provided in encrypted form as part of a data set, the method comprising:
encrypting a first item by a processor using both a first encryption key string that identifies said specific individual, and public data of a first trusted authority competent in respect of professional accreditations; and
encrypting a second item by a processor using both a second encryption key string that identifies said specific organization, and public data of a second trusted authority competent in respect of accreditations of organizations; and
forming said data set using at least the encrypted first and second items;
recovery of the target data in clear requiring decryption of both the first and second items.

7. An apparatus for the secure provision of target data to a party purporting to be a specific, professionally-accredited, individual engaged by a specific accredited organization, the apparatus comprising:
a processor encryption subsystem for generating a data set including the target data in encrypted form;
first encryption means for encrypting a first item, according to an Identifier-Based Encryption, IBE, scheme, based on encryption parameters comprising a first encryption key string that identifies said specific individual, and public data of a first trusted authority competent in respect of professional accreditations;
second encryption means for encrypting a second item, according to an IBE scheme, based on encryption parameters comprising a second encryption key string that identifies said specific organization, and public data of a second trusted authority competent in respect of accreditations of organizations; and
means for forming the data set using at least the encrypted first and second items; the recovery of the target data in clear requiring decryption of both the first and second items.

8. The apparatus according to claim 7, wherein the first item comprises the target data, and the second item comprises the encrypted first item.

9. The apparatus according to claim 7, wherein the first item comprises the target data, and the second item comprises a nonce; the first encryption key string comprising, in combination, an identifier of said specific individual and said nonce.

10. The apparatus according to claim 7, wherein the first item comprises first data, and the second item comprises second data; the data set further comprising said target data encrypted using a symmetric key that can be formed by using both said first and second data.

11. The apparatus according to claim 7, wherein the data set comprises, in addition to said first and second items, said target data encrypted using a first symmetric key, the second item comprising a second symmetric key, and the first item comprising the first symmetric key encrypted using the second symmetric key.

12. A computing entity for recovering target data provided in encrypted form as part of an data set that comprises first and second encrypted items both of which must be decrypted to recover the target data, the first item being encrypted in dependence on encryption parameters comprising a first encryption key string that identifies a specific individual and first public data, and the second item being encrypted in dependence on a second encryption key string that identifies a specific organization and second public data; the entity comprising:
  a processor-based system comprising;
  first means for requesting either a first decryption key corresponding to the first encryption key string, or the first item in decrypted form, from a first trusted authority and holds first private data related to the first public data, the first means being arranged to provide the first encryption key string to the first trusted authority when making its request and being further arranged to authenticate the entity with the first trusted authority and to receive the first decryption key, or the first item, securely from the first trusted authority;
  second means for requesting either a second decryption key corresponding to the second encryption key string, or the second item in decrypted form, from an organization accredited by a second trusted authority which holds second private data related to the second public data, the second means being arranged to provide the second encryption key string to the organization when making its request and being further arranged to authenticate the entity with the organization and receive the second decryption key, or the second item, from the organization;
  third means for using the first decryption key, or the first item, provided by the first trusted authority and the second decryption key, or the second item, provided by the organization, to recover the target data.

13. The computing entity according to claim 12, wherein the second means is arranged to receive the second decryption key, or the second item, securely from the organization.

14. The computing entity according to claim 12, wherein the first item comprises the target data, and the second item comprises the encrypted first item; the third means being arranged to recover the second item, if not provided to the second means in decrypted form by the organization, by using the second decryption key obtained from the organization, and subject the second item to decryption, using the first decryption key obtained from the first trusted authority, to recover the target data (0077; 0082).

15. The computing entity according to claim 12, wherein the first item comprises the target data, the second item comprises a nonce, and the first encryption key string comprises, in combination, an identifier of said specific individual and said nonce; the third means being arranged to: recover the second item, if not provided to the second means in decrypted form by the organization, by using the second decryption key obtained from the organization, combine the nonce that formed the second item with the identifier of said specific individual in order to form the first encryption key string to be provided by the first means to the first trusted authority and use the first decryption key obtained from the first trusted authority to decrypt the first item and thereby recover the target data.

16. The computing entity according to claim 12, wherein the first item comprises first data and the second item comprises second data, the data set further comprising said target data encrypted using a symmetric key that can be formed by using both said first and second data; the third means being arranged to recover the first data, if not provided to the first means by the first trusted authority, by using the first decryption key obtained from the first trusted authority, recover the second data, if not provided to the second means in decrypted form by the organization, by using the second decryption key obtained from the organization, use the first data and the second data to form said symmetric key, and use the symmetric key to decrypt the target data.

17. The computing entity according to claim 12, wherein the data set comprises, in addition to said first and second items, said target data encrypted using a first symmetric key, the second item comprising a second symmetric key, and the first item comprising the first symmetric key encrypted using the second symmetric key; the third means being arranged to: recover the first item, if not provided to the first means by the first trusted authority, by using the first decryption key obtained from the first trusted authority, recover the second item, if not provided to the second means in decrypted form by the organization, by using the second decryption key obtained from the organization, use the second symmetric key that formed the second item to decrypt the encrypted first symmetric key that formed the first item, and use the first symmetric key to decrypt the encrypted target data.

18. A computing entity for recovering target data provided in encrypted form as part of an data set that comprises first and second encrypted items both of which must be decrypted to recover the target data; the first item being encrypted in dependence on a first encryption key string that identifies a specific individual, and first public data; and the second item being encrypted in dependence on a second encryption key that identifies a specific organization and said specific individual, and second public data; the entity comprising:
  a processor-based system comprising;
  first means for requesting either a first decryption key corresponding to the first encryption key, or the first item in decrypted form, from a first trusted authority which is competent in respect of the accreditation of professionals and holds first private data related to the first public data, the first means being arranged to provide the first encryption key string, or the first item, to the first trusted authority when making its request;
  second means for requesting either a second decryption key corresponding to the second encryption key string, or the second item in decrypted form, from an organization accredited by a second trusted authority which holds second private data related to the second public data, the second means being arranged to provide the second encryption key string to the organization when making its request; and third means for using the first decryption key, or the first item, provided by the first trusted authority and the second decryption key, or the second item, provided by the organization, to recover the target data;

at least one of the first means and the second means being arranged to authenticate the entity to the first trusted authority or said organization as the case may be and to receive input therefrom in a secure manner.

19. The computing entity according to claim 18, wherein computing entity, wherein the first item comprises the target data, and the second item comprises the encrypted first item; the third means being arranged to: recover the second item, if not provided to the second means in decrypted form by the organization, by using the second decryption key obtained from the organization, and subject the second item to decryption, using the first decryption key obtained from the first trusted authority, to recover the target data (0077; 0082).

20. The computing entity according to claim 18, wherein the first item comprises the target data, the second item comprises a nonce, and the first encryption key string comprises, in combination, an identifier of said specific individual and said nonce; the third means being arranged to: recover the second item, if not provided to the second means in decrypted form by the organization, by using the second decryption key obtained from the organization, combine the nonce that formed the second item with the identifier of said specific individual in order to form the first encryption key string to be provided by the first means to the first trusted authority, and use the first decryption key obtained from the first trusted authority to decrypt the first item and thereby recover the target data.

21. The computing entity according to claim 18, wherein the first item comprises first data and the second item comprises second data, the data set further comprising said target data encrypted using a symmetric key that can be formed by using both said first and second data; the third means being arranged to recover the first data, if not provided to the first means by the first trusted authority, by using the first decryption key obtained from the first trusted authority, recover the second data, if not provided to the second means in decrypted form by the organization, by using the second decryption key obtained from the organization, use the first data and the second data to form said symmetric key, and use the symmetric key to decrypt the target data.

22. The computing entity according to claim 18, wherein the data set comprises, in addition to said first and second items, said target data encrypted using a first symmetric key, the second item comprising a second symmetric key, and the first item comprising the first symmetric key encrypted using the second symmetric key; the third means being arranged to: recover the first item, if not provided to the first means by the first trusted authority, by using the first decryption key obtained from the first trusted authority, recover the second item, if not provided to the second means in decrypted form by the organization, by using the second decryption key obtained from the organization, use the second symmetric key that formed the second item to decrypt the encrypted first symmetric key that formed the first item, and use the first symmetric key to decrypt the encrypted target data.

* * * * *